United States Patent [19]

Diehl et al.

[11] 4,086,242

[45] Apr. 25, 1978

[54] 1H- AND 2H-BENZOTRIAZOLES

[75] Inventors: Robert Eugene Diehl, Lawrenceville, N.J.; Roger Vernon Kendall, Pasadena, Calif.

[73] Assignee: American Cyanamid Company, Stamford, Conn.

[21] Appl. No.: 761,098

[22] Filed: Jan. 12, 1977

Related U.S. Application Data

[63] Continuation-in-part of Ser. No. 490,526, Jul. 22, 1974, abandoned.

[51] Int. Cl.² ............................................ C07D 249/18
[52] U.S. Cl. ..................................... 260/308 B; 71/92
[58] Field of Search ...................................... 260/308 B

[56] References Cited

FOREIGN PATENT DOCUMENTS 990,111  4/1965  United Kingdom ............ 260/308 B

OTHER PUBLICATIONS

Picci et al., Chemical Abstracts, vol. 68, 77089x.

*Primary Examiner*—Paul M. Coughlan, Jr.
*Attorney, Agent, or Firm*—Bruce F. Jacobs

[57] ABSTRACT

This invention relates to novel 1H- and 2H-benzotriazoles. These benzotriazoles are useful as herbicidal agents for the control of undesirable broadleaf weeds and grass weeds and may be applied to the foliage of undesirable plants or to soil containing seeds of said undesirable plants in order to obtain the control thereof.

16 Claims, No Drawings

1H- AND 2H-BENZOTRIAZOLES

CROSS REFERENCE TO RELATED APPLICATIONS

This is a continuation-in-part of copending application Ser. No. 490,526 filed July 22, 1974, now abandoned. Applicants' copending application Ser. No. 490,422 filed July 22, 1974, now abandoned, claims the use of benzotriazoles as herbicides.

BACKGROUND OF THE INVENTION

1. Field of the Invention

The invention pertains to new benzotriazole chemical compounds.

2. Description of the Prior Art

Compounds such as 1-methyl-4-nitro-1H-benzotriazole and 1-methyl-5-nitro-1H-benzotriazole are taught in C.A. 60 · 12004d. 1-Methyl-4-nitro-1H-benzotriazole is included in Tables III and V below for comparison. The compound 4-nitro-1H-benzotriazole is within the generic disclosure of Japanese patent application show a 44-49635 dated June 23, 1969 (showa 44), applicant Nitto Chemical Industrial Company 1-5-1, Marunouchi, ChiyodaKu, Tokyo. The compound is included in Table III and V for comparison. The Japanese patent teaches the use as a soil additive which decreases nitrate formation.

SUMMARY OF THE INVENTION

This invention relates to novel 1H-benzotriazoles and 2H-benzotriazoles represented by the formulas:

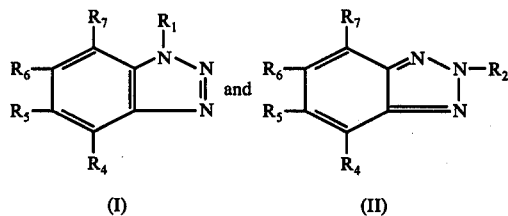

wherein $R_1$ and $R_2$ each independently represent a secondary alkyl $C_3$-$C_7$; tertiary alkyl $C_4$-$C_7$; acyloxy $C_1$-$C_3$; benzyl; cycloalkenyl $C_3$-$C_8$; —(CH$_2$)$_n$-cycloalkyl($C_3$-$C_8$), optionally substituted with a hydroxy, alkoxy $C_1$-$C_3$, alkyl $C_1$-$C_3$ or

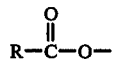

wherein R is $C_1$-$C_2$ alkyl and $n$ is 0 or 1; cyclohexylone;

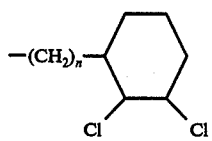

where $n$ is 0 or 1; $R_4$ represents hydrogen, halogen, cyano, methoxy or nitro; $R_5$ and $R_6$ are both hydrogen or both methyl; $R_7$ is hydrogen or nitro; with the proviso that when $R_4$ is nitro, halogen, methoxy or cyano, then $R_5$, $R_6$ and $R_7$ are each hydrogen and when $R_4$ is hydrogen then $R_7$ is nitro and $R_5$ and $R_6$ are each methyl.

The 1H-benzotriazoles of formula I, wherein $R_1$ is as described above, $R_4$ is nitro and $R_5$, $R_6$ and $R_7$ are hydrogen, are generally preferred, and most preferred of these compounds are those in which $R_1$ is cycloalkenyl $C_3$-$C_8$; —(CH$_2$)$_n$-cycloalkyl($C_3$-$C_8$) optionally substituted with a hydroxy, alkoxy $C_1$-$C_3$ alkyl $C_1$-$C_3$, or

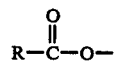

wherein R is $C_1$-$C_2$ alkyl and $n$ is 0 or 1; cyclohexylone or

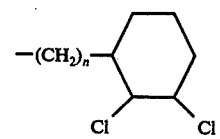

where $n$ is 0 or 1. Other preferred 1-H-benzotriazoles are those in which $R_1$ is secondary alkyl $C_3$-$C_7$ and, finally, $R_1$ is benzyl.

DETAILED DESCRIPTION AND PREFERRED EMBODIMENTS

The compounds of the invention may be prepared by several different methods. The procedure employed depends upon the substituents present in the benzotriazole ring and also upon whether the benzotriazole is a 1H-benzotriazole or a 2H-benzotriazole.

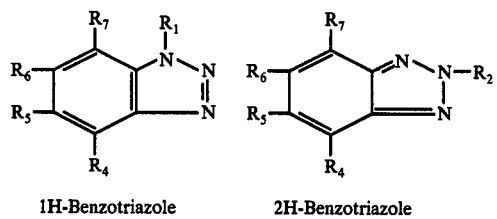

1H-Benzotriazole      2H-Benzotriazole

The 1-alkyl-1H-and 2-alkyl-2H-benzotriazoles of the present invention may be prepared by the alkylation of the appropriate benzotriazole, either substituted or unsubstituted in the benzene ring, with an appropriate alkylating agent. The alkylating agent may be selected from the appropriate secondary or cyclic saturated or unsaturated aliphatic alkyl bromides and iodides containing from 3 to 8 carbon atoms. The reaction may be carried out by heating a mixture of the benzotriazole, a strong base such as an alkali metal hydroxide or alkali metal alkoxide, the alkylating agent and an organic solvent such as acetonitrile, dimethylformamide, dimethoxyethane, dimethyl sulfoxide, nitromethane or a lower alkyl $C_1$-$C_4$ ketone at a temperature of generally between 50° C. and 100° C. The reaction for 4-nitrobenzotriazole is illustrated below.

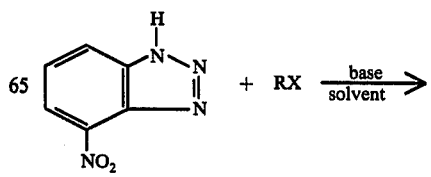

-continued

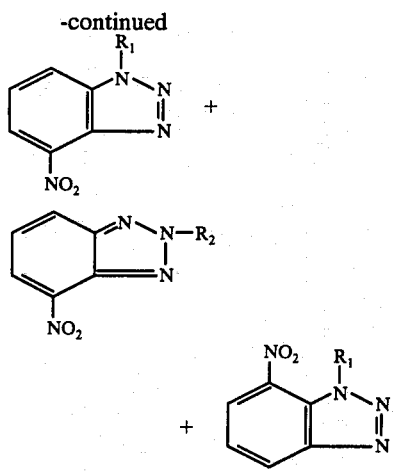

The 1-alkyl-1H-benzotriazoles can be separated from the 2-alkyl-2H-benzotriazole by an extraction with concentrated hydrochloric acid, or hydrobromic acid. The 2H-benzotriazole is insoluble in the acid whereas the 1H-benzotriazoles are soluble. Separation of the 1-alkyl-4-nitro isomer and 1-alkyl-7-nitro isomer can be accomplished by fractional recrystallization, chromatography or by an extraction of the 1-alkyl-4-nitrobenzotriazole with concentrated hydrochloric acid from a benzene or chloroform solution of the two isomers.

The 4-nitrobenzotriazole can be prepared by the nitration of the parent benzotriazole in a 90% nitric —23% oleum medium. The reaction is usually conducted at a temperature below 50° C. with an excellent product yield being obtained.

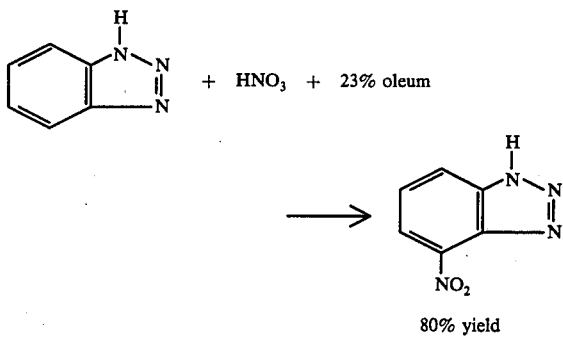

The 1H-benzotriazoles may also be prepared in a three step synthesis from 1-chloro-2-nitrobenzene and an appropriate amine.

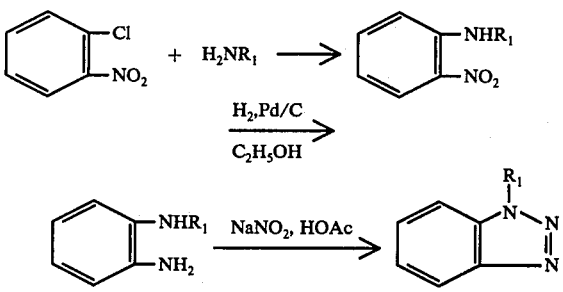

The first step is conveniently carried out by refluxing 1 part of the 1-chloro-2-nitrobenzene with one to three parts of a primary amine ($R_1 = C_3$ to $C_8$, branched or cyclic aliphatic chains for several hours to several days depending on the amine. The reduction of the nitro group in the second step is readily accomplished via a catalytic hydrogenation with hydrogen and 10% palladium or platinum on carbon in a $C_1-C_4$ alcoholic solution. The third step may be carried out by adding an aqueous solution of sodium or potassium nitrite to a dilute hydrochloric acid, acetic acid or other carboxylic acid solution of the phenylenediamine. This reaction is generally carried out at about 25° C. to 30° C.

The 1-alkyl-5,6-dimethyl-7-nitrobenzotriazoles may be prepared from the 5,6-dimethyl 2,6-dinitrochlorobenzene. The reaction is graphically illustrated as follows:

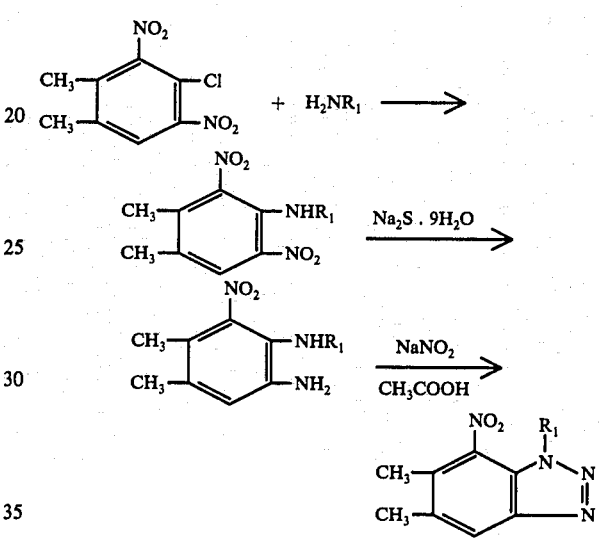

The procedure is essentially the same as the procedure described for preparing the 1-alkylbenzotriazoles except an alkali metal sulfide such as sodium sulfide is used to prepare the phenylenediamine.

A third procedure involves the nitration of the 1H-alkylbenzotriazoles in a 90% nitric acid —23% oleum medium (1:2 ratio) which yields all four possible nitration product. The major product of the reaction is the 1-alkyl-4-nitrobenzotriazole. The nitration is generally carried out at a temperature of about 25° C. and is graphically illustrated as follows.

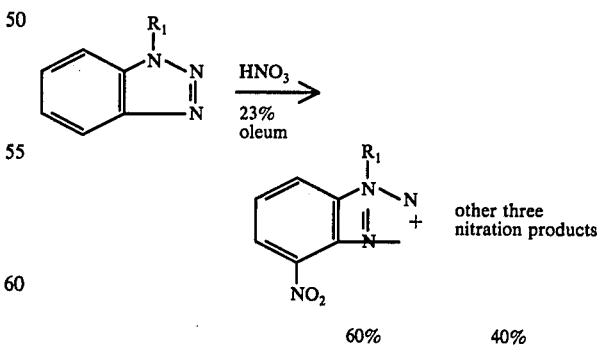

Benzotriazoles substituted in the benzene ring can also be nitrated by this procedure.

Nitration of the 2H-benzotriazoles can not be accomplished in the nitric acid-oleum medium since the sulfuric acid promotes the cleavage of the alkyl group. An exception is the 2-methylbenzotriazoles which are stable to the sulfuric acid. The nitration can be accomplished, however, with a 90% nitric acid-acetic anhydride medium which yields a 60:40 mixture of the two possible nitration products. This reaction is also generally conducted at a temperature below 25° C. and preferably between about 10° C. and 15° C. The reaction is graphically illustrated as follows:

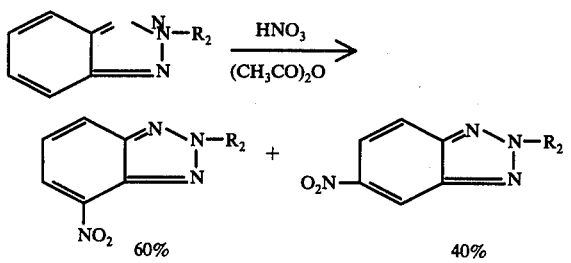

4-Nitrobenzotriazole can also be alkylated with cyclohexene oxide to yield the cyclohexanol derivatives. The reaction can be carried out in refluxing acetonitrile using sodium hydroxide to generate the anion of the benzotriazole. Two of the possible three isomers are isolated from the reaction.

Formylation of the hydroxy group of the 2-(4-nitro-1H-benzotriazol-1-yl)-cyclohexanol can be accomplished with thionyl chloride in DMF.

Besides nitro, additional 4-substituted 1-cyclohexylbenzotriazoles have been prepared. For instance, the reduction of the nitro group in 4-nitrobenzotriazoles is readily accomplished in ethanol by using 10% palladium on carbon as the catalyst.

The 4-amino-1-cyclohexylbenzotriazole can be converted to the chloro and cyano derivatives in good yields through the formation of the diazonium salt (Sandmeyer reaction).

-continued

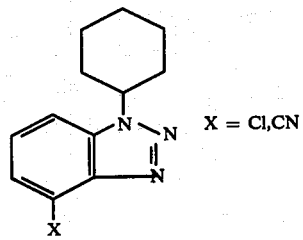

Displacement of the chloro group in 4-chloro-1-cyclohexylbenzotriazole by methoxide ion can be accomplished if cuprous iodide is added to the reaction. The reaction fails in absence of the copper salt.

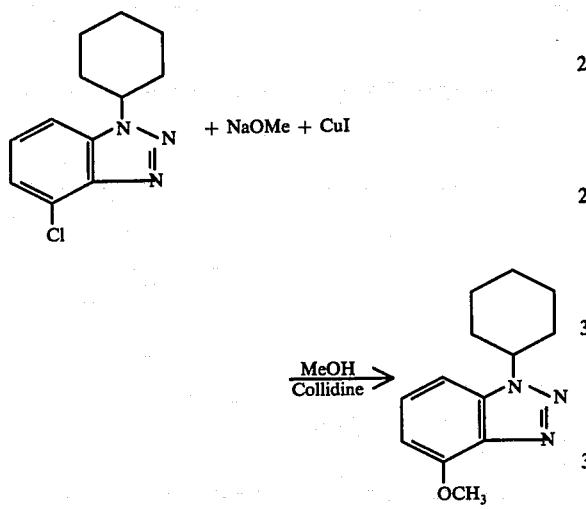

Herbicides of the benzotriazole class may be formulated as dusts, wettable powders, granulars, and flowables.

A dust formulation can be prepared by grinding the toxicant with a suitable inert diluent such as clay (attapulgite, kaolin, etc.), diatomaceous earth, talc, or any other finely ground nonreactive organic or inorganic diluent. The potency of the dust may vary by 1 to 99%, depending upon the desired use for the product.

A wettable powder formulation can be prepared by blending the toxicant with an inert diluent (clay, talc, corn cob, etc.) dispersing agent (lignin sulfonate or neutral sodium salts of condensed aryl sulfonic acids), and if necessary, a wetting agent such as alkyl aryl polyethylene glycols or the dioctyl ester of sodium sulfosuccinic acid. The blended material is then ground in a suitable attrition mill until the desired particle size range is achieved. The usual concentration of a wettable powder is 50 to 80% toxicant, but higher or lower concentrations may be prepared. The dispersing agent is usually employed at the 5% level and the wetting agent from 1 to 2%. The inert diluent is used to make up the balance to 100%.

Flowable preparations of the herbicides can be prepared by grinding the toxicant, dispersing agent, wetting agent inert diluent, in a solvent, e.g., water. The grinding is done by using a suitable attrition mill such as a ball mill or colloid mill.

The inert diluent, as well as the dispersing and wetting agents may be the same as those used in the wettable powder. A thickening agent, organic (hydroxy-methyl cellulose) or inorganic (bentonite), may be used to increase the viscosity of the liquid. The potency of the flowable can vary from 10 to 70% with 50% being a reasonable concentration.

Granular preparation of the benzotriazoles can be prepared by impregnation. In impregnation, the compound is dissolved in a suitable solvent, volatile or non-volatile, e.g., methylene chloride, acetone, or a heavy aromatic solvent such as Panasol® AN-2 or the like and the solution sprayed onto the clay. If it is desired, a wetting agent such as an alkyl aryl polyethylene glycol may be added to the spray solution. The solvent is then removed or allowed to remain on the thus prepared granular product. The concentration of the active agent on the granular carrier may range from 1 to 30% w/w with 3% being a practical level.

The invention is further demonstrated by the examples set forth below:

EXAMPLE 1

Preparation of 1-sec-Butyl-1H-benzotriazole and 2-sec-Butyl-2H-benzotriazole

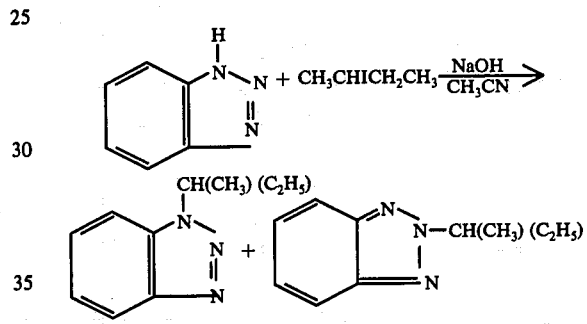

To a stirred solution of 96.0 g. of benzotriazole in 800 ml. of acetonitrile at 50° C. is added 33.6 g. of sodium hydroxide pels. After most of the sodium hydroxide has reacted with the benzotriazole, 190 g. of 2-iodobutane is added in one portion and the resulting solution is refluxed for 15 hours. The acetonitrile is then evaporated and 300 ml. of concentrated hydrochloric acid is added to the residual oil followed by the addition of 800 ml. of benzene. The precipitated sodium iodide is removed by filtration. The acid layer is separated from the benzene layer and then washed three more times with 300 ml. of benzene. The benzene washings are combined, dried over $MgSO_4$ and evaporated to yield 48 g. (34%) of the 2-sec-butyl-2H-benzotriazole as an oil. The material is purified by distillation, b.p. 0.25 mm Hg=63° C.

Analysis Calcd. for $C_{10}H_{13}N_3$: C, 68.54; H, 7.48; N, 23.98. Found C, 68.90; H, 7.62; N, 24.19.

To isolate the 1-sec-butyl isomer, the concentrated hydrochloric acid layer is added to 1200 ml. of ice water. The product oils out and is then extracted with chloroform. The chloroform is dried over $MgSO_4$ and evaporated to yield 69 g. (50%) of the 1-sec-butyl benzotriazole. The product is purified by distillation, b.p. 1.0 mm Hg = 145°-149° C.

Analysis Calcd. for $C_{10}H_{13}N_3$: C, 68.54; H, 7.48; N, 23.98. Found: C, 68.71; H, 7.51; N, 24.15.

Slightly higher yields of the two products are obtained when alkyl bromide is used in place of the alkyl iodide.

EXAMPLE 2

Preparation of N-(1-Ethylpropyl)-o-nitroaniline

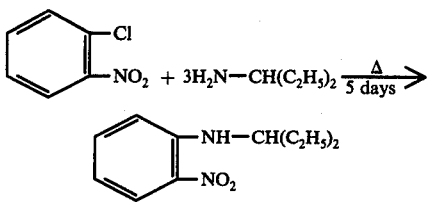

A solution of 158 g. of 1-chloro-2-nitrobenzene and 260 g. of 1-ethyl propylamine are refluxed together for 5 days. The solution is cooled and 500 ml. of water is added followed by 10 ml. of concentrated hydrochloric acid. The product separates out as an oil and is extracted with chloroform (2 × 200 ml.). The chloroform layer is dried over $MgSO_4$ and evaporated to yield 190 g. (91%) of product.

The analytical sample is prepared by distillation of the crude oil, b.p. 1.8 mm Hg=148° C.

Analysis Calcd. for $C_{11}H_{16}N_2O_2$: C, 63.44; H, 7.75 N, 13.45. Found: C, 63.16; H, 7.82; N, 13.16.

EXAMPLE 3

Preparation of N-(1-Ethylpropyl)-o-phenylenediamine

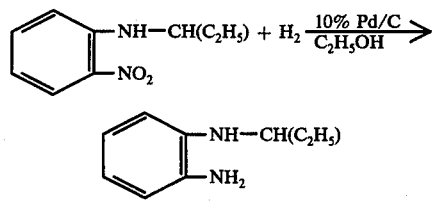

In a 2 liter hydrogenator is placed 2.5 g. of 10% palladium on carbon catalyst, 800 ml. of absolute alcohol and 250 g. of o-nitro-N-(1-ethylpropyl) aniline. Hydrogen is introduced and the reduction is complete in about 2½ hours. The reaction is exothermic and the temperature subsides as the reaction goes to completion. The catalyst is removed by filtration and the ethanol is evaporated to yield a nearly quantitative yield (214 g.) of product as a dark oil. A pure sample is obtained by vacuum distillation, b.p. 2.0 mm Hg=125°-126° C.

EXAMPLE 4

Preparation of 1-(1-Ethylpropyl)-1H-benzotriazole

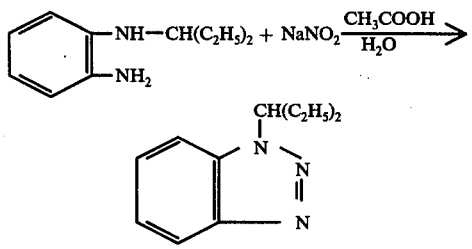

To a solution of the phenylenediamine (23.6 g.) in 120 ml. of acetic acid cooled to 15° C. is slowly added 10.2 g. of $NaNO_2$ in 50 ml. of water. During the addition, the reaction temperature is not allowed to exceed 30° C. On completion of the addition, the reaction mixture is stirred an additional one hour at room temperature and then 50 ml. of dichloroethane is added followed by 100 ml. of water. The organic phase is separated, washed with a saturated sodium bicarbonate solution (50 ml.) and then washed with 50 ml. of water. The organic phase is dried over $Na_2SO_4$ and the solvent is evaporated to yield 15.8 g. (84%) of a dark liquid. The compound is purified by distillation, b.p. 1.7 mm Hg ca 139° C.

Analysis Calcd. for $C_{11}H_{15}N_3$: C, 69.81; H, 7.99; N, 22.20. Found: C, 69.15; H, 8.14; N, 21.97.

EXAMPLE 5

Preparation of 1-(Ethylpropyl)-4-nitro-1H-benzotriazole

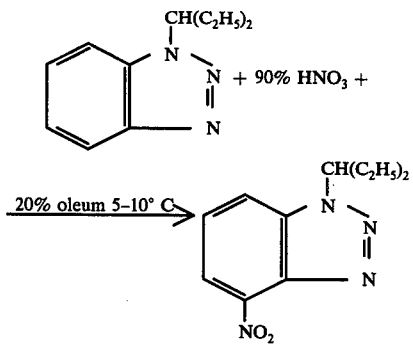

Over a 2½ hour period, 210 g. of the 1-(1-ethylpropyl)benzotriazole is added to a mixture of 100 ml. of 90% nitric acid and 400 ml. of 23% oleum with stirring. The mixed acid solution is cooled in an ice-salt bath and the addition rate is such that a temperature of between 5°-10° C. is maintained. The reaction mixture is maintained at 5°-10° C. for an additional 1½ hours, and then at 25° C. for one more hour. The reaction mixture is then poured over 2500 g. of ice with stirring. After 15 minutes of stirring, the brown precipitate is collected by filtration, washed with additional water and air dried. The crude product is then slurried with 500 ml. of 95% ethanol and then a second time with an additional 400 ml. of hot 95% ethanol. The slurry is cooled and product is collected by filtration and dried to yield 108.5 g. (45%) of brown solid, m.p. 129°-132° C. The analytical sample is recrystallized from chloroform-petroleum ether to give m.p. 132°-134° C.

Analysis Calcd. for $C_{11}H_{14}N_4O_2$: C, 56.40; H, 6.02; N, 23.92. Found: C, 56.38; H, 6.02; N, 24.27.

EXAMPLE 6

Preparation of 2-sec-Butyl-4-nitro-2H-benzotriazole and 2-sec-Butyl-5-nitro-2H-benzotriazole

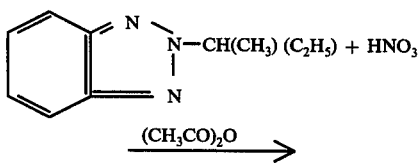

-continued

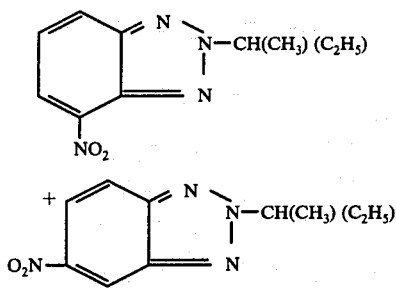

Over a period of 1 hour, 10.2 g. of 90% nitric acid is added to 5.0 g. 2-sec-butylbenzotriazole in 50 ml. of acetic anhydride at 0° C. The reaction is stirred at room temperature for an additional 3 hours and then poured over 200 g. of ice and water. Then 200 ml. of chloroform is added and with stirring 10% sodium hydroxide is added until the aqueous layer is quite basic. The chloroform layer is dried over $MgSO_4$ and evaporated to yield 5.0 g. of an oil (mixture of the two nitration products). The two nitration products are separated on a silica gel dry column using chloroform as the eluant. Structure elucidation is based on comparison of their nmr spectra. The 2-sec-butyl-4-nitro benzotriazole is analyzed for $C_{10}H_{12}N_4O_2$: C, 54.33; H, 5.49; N, 25.44 Found: C, 54.30; H, 5.39; N, 25.44.

The 2-sec-butyl-5-nitro benzotriazole is analyzed for $C_{10}H_{12}N_4O_2$: C, 54.33; H, 5.49; N, 25.44. Found: C, 54.80; H, 5.69; N, 25.66.

EXAMPLE 7

Preparation of 4-Nitro-1H-benzotriazole

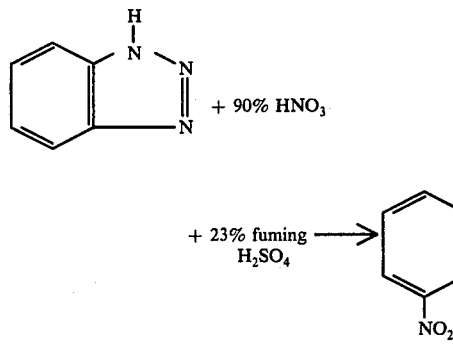

To a cooled solution (20° C.) of 1,060 ml. of 23% fuming sulfuric acid and 265 ml. of 90% nitric acid is added in a dropwise fashion a solution of 537 g. of benzotriazole in 1000 ml. of concentrated sulfuric acid. The temperature is not allowed to go above 50° C. At the end of the addition, the reaction mixture is allowed to stand at room temperature overnight. The reaction mixture is then poured over ice and water and a heavy yellow precipitate forms. The solid is collected by filtration, washed with water and dried. The solid, which is a mixture of the 4-nitro (90%) and the 5-nitro (10%) products, is then slurried with 7.5 l. of hot acetonitrile cooled and 537 g. (73%) of 4-nitrobenzotriazole is collected by filtration, m.p. 228°-231° C.

EXAMPLE 8

Preparation of 1-Isopropyl-4-nitro-1H-benzotriazole and 2-Isopropyl-4-nitro-2H-benzotriazole

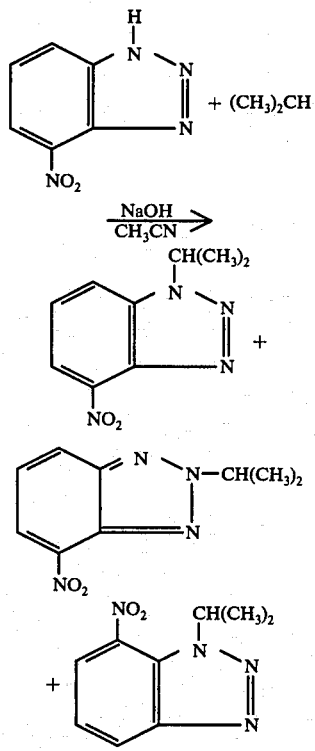

To a hot, stirred solution (50° C) of 20.0 g. of 4-nitrobenzotriazole in 600 ml. of acetonitrile is added 4.2 g. of sodium hydroxide pels and 20.0 g. of isopropyl iodide. The solution is then heated to reflux for 30 hours, filtered and the solvent removed by evaporation to yield an oil. The oil is extracted with concentrated hydrochloric acid (3 × 200 ml.) to leave behind a solid material. The solid is washed with water and air dried to yield crude 2-isopropyl-4-nitrobenzotriazole. The analytical sample is recrystallized from petroleum ether, m.p. 65°-67° C.

Analysis Calcd. for $C_9H_{10}N_4O_2$: C, 52.42; H, 4.89; N, 27.17. Found: C, 52.58; H, 4.88; N, 27.47.

To the acid filtrate is then added 1 liter of water and the aqueous mixture is extracted with ethyl ether (3 × 200 ml.). The ethyl ether is dried over $MgSO_4$ and as the solvent is evaporated, the 1-isopropyl-4-nitrobenzotriazole crystallizes from solution. The product is collected by filtration and air dried. The analytical sample is recrystallized from ethyl ether, m.p. 99°-100° C.

Analysis Calcd. for $C_9H_{10}N_4O_2$: C, 52.42; H, 4.89; N, 27.17. Found: C, 52.00; H, 4.87; N, 27.20.

EXAMPLES 9–23

Other 1H-benzotriazoles of the present invention can be prepared by the procedures heretofore described. These benzotriazoles are listed in Table I below where they are characterized by melting points. The procedure used for synthesis of each compound is identified by example number and each compound is prepared by substituting the appropriate intermediates into the procedure of the example identified.

TABLE I
1H-BENZOTRIAZOLES
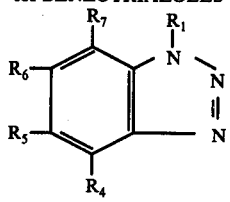
| Example No. | R₁ | R₄ | R₅ | R₆ | R₇ | °C. m.p. | Example Procedure |
|---|---|---|---|---|---|---|---|
| 9 | cycloheptyl | NO₂ | H | H | H | 109–111 | 5 |
| 10 | —CH₂-cyclohexyl | NO₂ | H | H | H | 101–102 | 8 |
| 11 | cyclohexenyl | NO₂ | H | H | H | 131–132 | 8 |
| 12 | —CH₂-phenyl | NO₂ | H | H | H | 123–125 | 8 |
| 13 | CH(CH₃)(C₂H₅) | NO₂ | H | H | H | 78–79 | 5 |
| 14 | —C(CH₃)₃ | NO₂ | H | H | H | 179–180 | 5 |
| 15 | CH(CH₃)(C₃H₇) | NO₂ | H | H | H | 69–70 | 5 |
| 16 | CH(C₃H₇)₂ | NO₂ | H | H | H | 49.5–50.5 | 5 |
| 17 | cyclohexyl | NO₂ | H | H | H | 163–165 | 5 |
| 18 | cyclopentyl | NO₂ | H | H | H | 80–81 | 8 |
| 19 | cyclopropyl | NO₂ | H | H | H | 160–163 | 5 |
| 20 | 2-methylcyclohexyl | NO₂ | H | H | H | 105–107 | 5 |
| 21 | 4-methylcyclohexyl | NO₂ | H | H | H | 152–154 | 5 |
| 22 | cyclooctyl | NO₂ | H | H | H | 82–84 | 8 |

TABLE I-continued

1H-BENZOTRIAZOLES

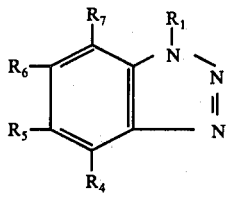

| Example No. | R₁ | R₄ | R₅ | R₆ | R₇ | °C. m.p. | Example Procedure |
|---|---|---|---|---|---|---|---|
| 23 | (2-oxocyclohexyl) | NO₂ | H | H | H | 203–205 | 8 |

EXAMPLES 24–32

Preparation of 2H-Benzotriazoles

Other 2H-benzotriazoles that can be prepared in accordance with process of the present invention are listed in Table II below. Melting points for compounds prepared are listed in said table along with the example number of the procedure used to prepare said compound.

TABLE II

2H-BENZOTRIAZOLES

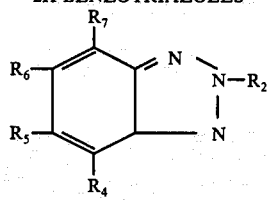

| Example No. | R₂ | R₄ | R₅ | R₆ | R₇ | °C. m.p. or b.p. | Example Procedure |
|---|---|---|---|---|---|---|---|
| 24 | cyclopentyl | NO₂ | H | H | H | 60–62 | 8 |
| 25 | −CH₂−cyclohexyl | NO₂ | H | H | H | 131–133 | 8 |
| 26 | CH(CH₃)₂ | NO₂ | CH₃ | CH₃ | H | 111–112 | 6 |
| 27 | cyclohexenyl | NO₂ | H | H | H | 88.5–89.5 | 8 |
| 28 | −CH₂−phenyl | NO₂ | H | H | H | 91–93 | 8 |
| 29 | CH(C₂H₅)₂ | NO₂ | H | H | H | 90–92 | 8 |
| 30 | cyclohexyl | NO₂ | H | H | H | 78–81 | 6 |
| 31 | cyclooctyl | NO₂ | H | H | H | 90–91 | 8 |

TABLE II-continued
2H-BENZOTRIAZOLES

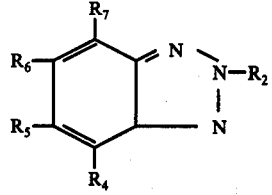

| Example No. | $R_2$ | $R_4$ | $R_5$ | $R_6$ | $R_7$ | °C. m.p. or b.p. | Example Procedure |
|---|---|---|---|---|---|---|---|
| 32 | (2-oxocyclohexyl) | $NO_2$ | H | H | H | 145–147 | 8 |

EXAMPLE 33

Preparation of
$N^4$-(1-Ethylpropyl)-3-nitro-o-xylene-4,5-diamine

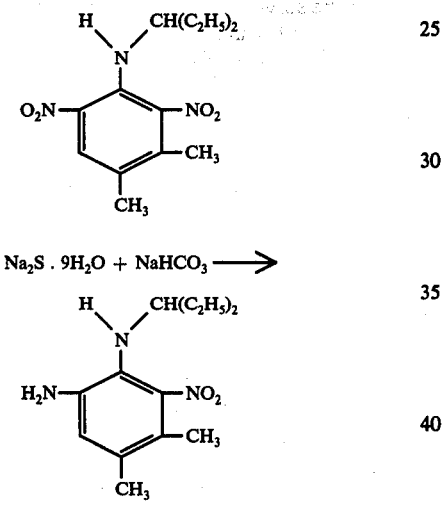

N-(1-Ethylpropyl)-2,6-dinitro-3,4-xylidine (100 g.) is dissolved in 2500 ml. of ethanol and a solution of sodium sulfide nonahydrate (240 g.) and sodium bicarbonate (84 g.) in 500 ml. of water is added at 25°–42° C. The mixture is heated to 65° C. and held at 60°–65° C. for 3 hours. The mixture is then poured into water and extracted 3 times with 1 liter portion of ether. The ether extracts are combined and dried over magnesium sulfate. Removal of the drying agent and solvent leaves a dark solid which is recrystallized 3 times from hexane and then 3 times from hexane-ethanol. The product (35.0 g.), an orange solid, has m.p. 80°–82° C. Analysis Calcd. for $C_{13}H_{21}N_3O_2$: C, 62.12; H, 8.41; N, 16.71. Found: C, 62.41; H, 8.33; N, 16.47.

EXAMPLE 34

Preparation of
$N^4$-sec-Butyl-3-nitro-o-xylene-4,5-diamine

Using the appropriate starting material, the title compound can be prepared following the procedure described for Example 33. The product is a red oil which crystallizes to a red solid with m.p. 36°–37° C. Analysis Calcd. for $C_{12}H_{19}N_3O_2$: C, 60.74; H, 8.07; N, 17.71. Found: C, 60.83; H, 8.23; N, 17.80.

EXAMPLE 35

Preparation of
1-(1-Ethylpropyl)-5,6-dimethyl-7-nitro-1H-benzotriazole

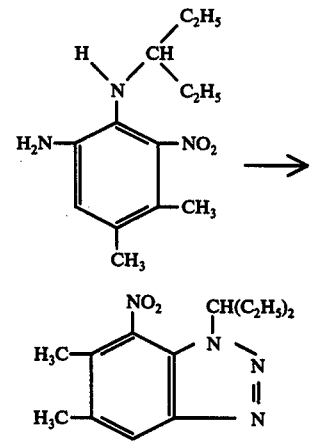

A sample of $N^4$-(1-ethylpropyl)-3-nitro-o-xylene-4,5-diamine (2.5 g.) is dissolved in 40 ml. of concentrated hydrochloric acid and filtered to remove some insoluble solid. The filtrate is diluted with 5–6 ml. of water and then chilled to 5° C. and held there while a sodium nitrite solution (0.69 g. in 10 ml. of water) is slowly added. When the addition is complete, the diazonium salt mixture is poured into boiling ethanol. After refluxing 10 minutes, the mixture is diluted with water and filtered. The crude solid (2.4 g.) is recrystallized from 15 ml. of methanol to give 1.55 g. with m.p. 106°–108.5° C. Analysis Calcd. for $C_{13}H_{18}N_4O_2$: C, 59.52; H, 6.92; N, 21.36. Found: C, 60.30; H, 7.21; N, 21.26.

EXAMPLE 36

Preparation of
1-sec-Butyl-5,6-dimethyl-7-nitro-1H-benzotriazole

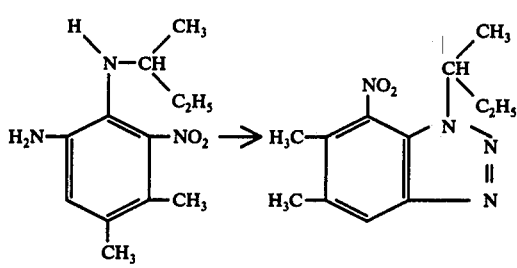

A solution of N⁴-(1-sec-butyl)-3-nitro-o-xylene-4,5-diamine (1.0 g.) in 14 ml. of glacial acetic acid and 2.0 ml. of water is stirred at 23°–28° C. while a sodium nitrite solution (0.3 g. in 2.0 ml. of H$_2$O) is added. After 15 minutes the solution is warmed to 40° C. On cooling the solution is diluted with a large volume of water.

The precipitated solid (0.9 g.) is collected and dried. Recrystallization from methanol-water gives 0.6 g. with m.p. 93°–96° C. Analysis Calcd. for C$_{12}$H$_{16}$N$_4$O$_2$: C, 58.05; H, 6.50; N, 22.57. Found: C, 57.81; H, 6.37; N, 22.45.

EXAMPLE 37

Preparation of
1-(2,3-Dichlorocyclohexyl)-4-nitro-1H-benzotriazole

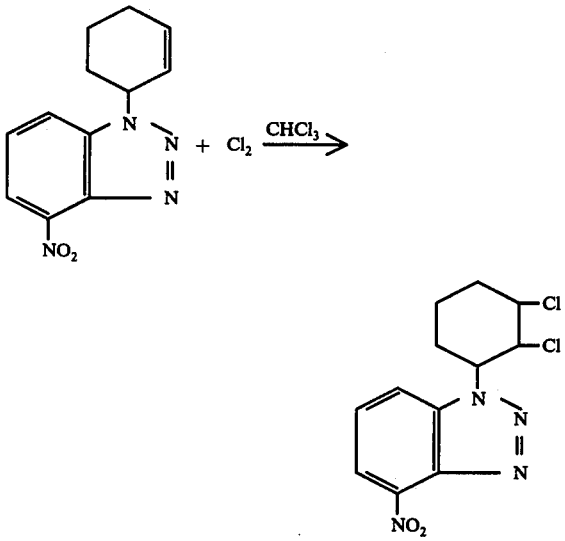

The benzotriazole is dissolved in chloroform and a 10–20% excess of chlorine gas is introduced to the stirred solution. The reaction is cooled in an ice bath as the reaction is exothermic. Then the reaction mixture is filtered through Hyflo ® to remove any insoluble material and the chloroform evaporated to yield the crude product. The material is recrystallized from chloroform-hexane, m.p. 145°–148° C.

Analysis Calcd. for C$_{12}$H$_{12}$N$_4$Cl$_2$O$_2$: C, 45.73; H, 3.84; N, 17.78; Cl, 22.50. Found: C, 45.62; H, 3.88; N, 17.55; C, 22.52.

EXAMPLE 38

Preparation of 4-amino-1-cyclohexyl-1H-benzotriazole

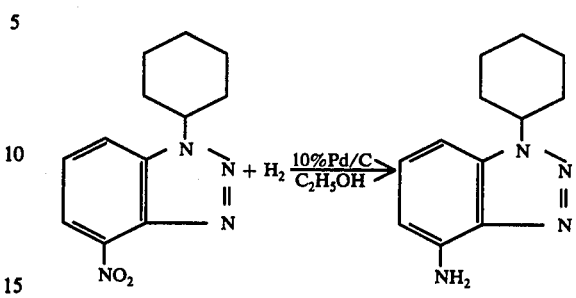

In a 500 ml. Paar hydrogenator is placed 49.2 g. of the 4-nitro-1-cyclohexyl-1H-benzotriazole, 220 ml. ethanol and 2.5 g. 10% palladium on carbon catalyst and the mixture is heated to 45° C. Hydrogen is introduced at about 40 psi and the temperature of the reaction is maintained at 60° C. The reaction is over after 1½ hours and the catalyst is then removed by filtration. On evaporation of the solvent, the product is isolated in quantitative yield as an oil, which solidifies on standing, m.p. 54°–60° C. Analysis Calcd. for C$_{12}$H$_{16}$N$_4$: C, 66.64; H, 7.46; N, 25.90. Found: C, 66.38; H, 7.55; N, 25.69.

EXAMPLE 39

Preparation of
4-Chloro-1-cyclohexyl-1H-benzotriazole

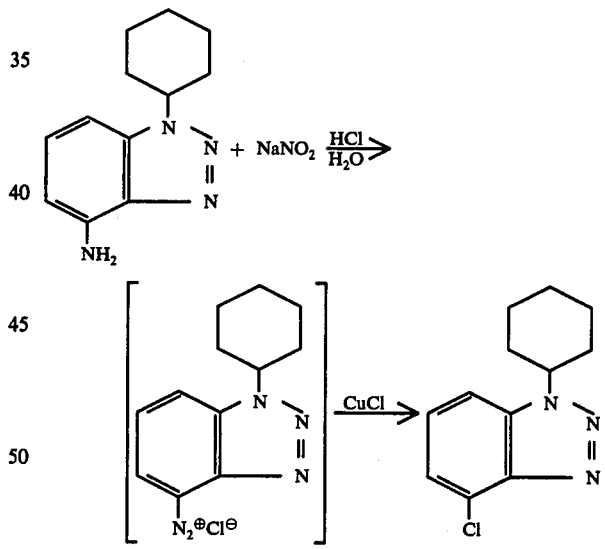

To a stirred solution of 11.4 g. of the 4-amino-1-cyclohexylbenzotriazole in 75 ml. of concentrated hydrochloric acid and 75 ml. of water kept at 5° C. is slowly added 4.1 g. of sodium nitrite in 15 ml. of water. On completion of the addition, the reaction mixture is allowed to stir an additional ½ hour at 0°–5° C. and then is added slowly to an excess of freshly prepared cuprous chloride in 120 ml. of concentrated hydrochloric acid also at 0°–5° C. On completion of the addition, the reaction is allowed to stir and come to room temperature over a 2½ hour period. Then 1000 ml. of water is added to the reaction mixture and the crude product is collected by filtration, washed with water and air dried. The product is purified by column chromatography, yield: 6.2 g, m.p. = 141°–144° C, analytical sample, m.p.=146°–147° C., is recrystallized from CHCl₃/Et₂O.

Analysis Calcd. for C₁₂H₁₄N₃Cl: C, 61.14; H, 5.99; N, 17.83; Cl, 15.04. Found: C, 60.93; H, 6.03; N, 17.83; Cl, 15.23.

EXAMPLE 40

Preparation of 4-Carbonitrile-1-cyclohexyl-1H-benzotriazole

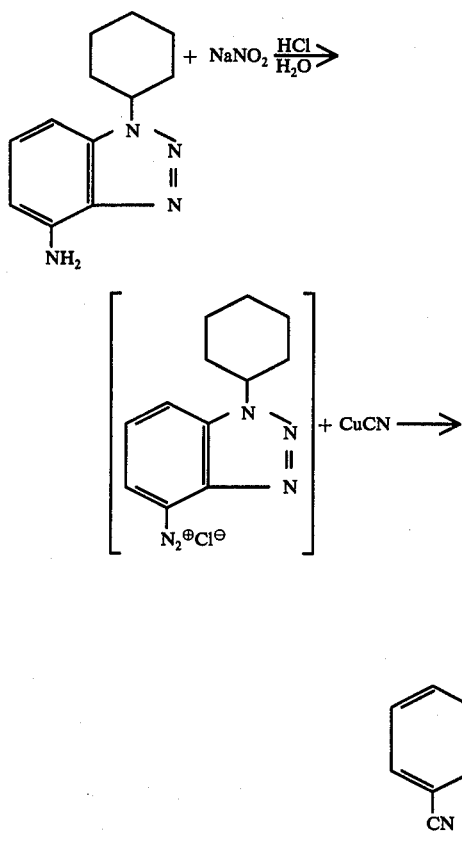

To a stirred solution of 10.2 g. of the 4-amino-1-cyclohexylbenzotriazole in 200 ml. H₂O and 50 ml. concentrate hydrochloric acid at 0°–5° C. is slowly added 3.6 g. of sodium nitrite in 20 ml. of water. After an additional ½ hour, 20 g. of sodium carbonate is slowly added to the reaction mixture to neutralize the acid. Being kept cold, the diazonium salt solution is then filtered and slowly added to an excess of freshly prepared cuprous cyanide solution in 200 ml. water and 150 ml. toluene at 0°–5° C. After standing at room temperature overnight, the reaction mixture is heated on the steam bath for 5–10 minutes. The toluene layer is separated, dried over magnesium sulfate and evaporated to yield 3.5 g. of a dark oily solid. The product is purified by dry column chromatography and the analytical sample is recrystallized from ethyl ether, m.p. 164°–165° C.

Analysis Calcd. for C₁₃H₁₄N₄: C, 69.00; H, 6.24; N, 24.76. Found: C, 69.21; H, 6.32; N, 25.03.

EXAMPLE 41

Preparation of 4-Methoxy-1-cyclohexyl-1H-benzotriazole

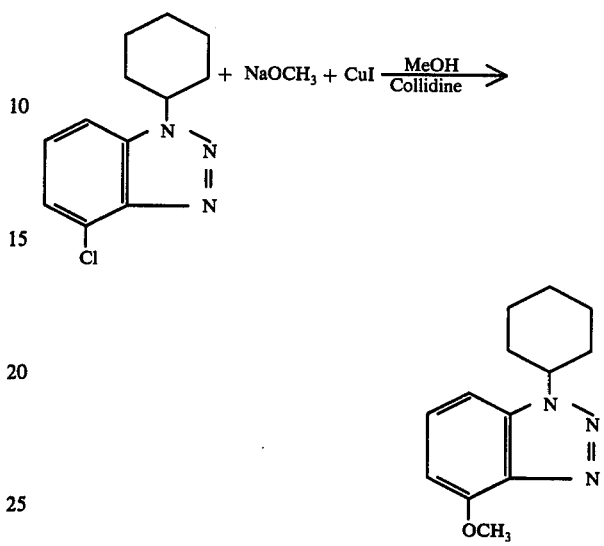

A slurry of 1.5 g. of 4-chloro-1-cyclohexylbenzotriazole, 15 g. of sodium methoxide, 10 g. cuprous iodide in 50 ml. of 2,4,6-trimethyl pyridine and 10 ml. of methanol is heated to the reflux temperature for 26 hours. The reaction is cooled and poured into 150 ml. of 10% hydrochloric acid. The product is extracted with ethyl ether and on evaporation of the solvent, 0.5 g. of an oil was obtained which solidified on standing. Recrystallized the crude product from ethyl ether, m.p. 118°–120° C. The analytical sample has a m.p. 133°–134° C.

Analysis Calcd. for C₁₃H₁₇N₃O: C, 67.51; H, 7.41; N, 18.17. Found: C, 67.77; H, 7.54; N, 18.37.

EXAMPLE 42

Preparation of 2-(4-Nitro-1H-benzotriazol-1-yl)-cyclohexanol and 2-(4-Nitro-2H-benzotriazol-2-yl)-cyclohexanol

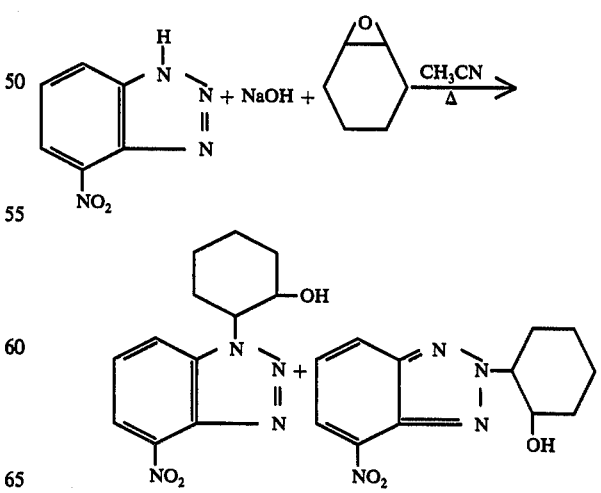

A mixture of 60 g. of 4-nitrobenzotriazole, 16 g. sodium hydroxide "Pels" and 1500 ml. of acetonitrile is heated to 60° C. The cyclohexene oxide is then slowly added and the solution is heated at the reflux temperature for 48 hours. After cooling, the reaction is filtered and the acetonitrile evaporated to yield an oily residue. The 2-alkyl isomer is extracted with ethyl ether leaving behind the 1-alkyl isomer as a crude solid.

The 1-alkyl isomer is recrystallized from methanol, m.p. 205°-206° C. Analysis Calcd. for $C_{12}H_{14}N_4O_3$: C, 54.96; H, 5.40; N, 21.36. Found: C, 54.95; H, 5.13; N, 21.54.

The 2-alkyl isomer is recrystallized from carbon tetrachloride, m.p. 139°-141° C. Analysis Calcd. for $C_{12}H_{14}N_4O_3$: C, 54.95; H, 5.40; N, 21.36. Found: C, 54.56; H, 5.19; N, 21.56.

EXAMPLE 43

Preparation of 2-(4-Nitro-1H-benzotriazol-1-yl)-cyclohexanol formate ester

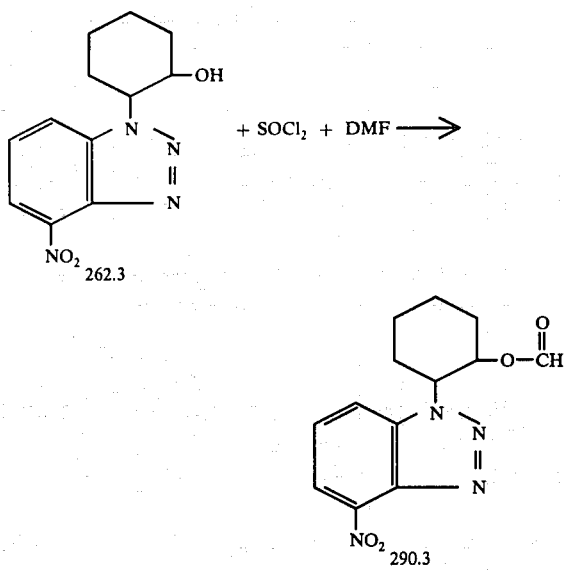

To a solution of 1.0 g. of the benzotriazole in 10 ml. of dimethylformamide is slowly added a mixture of 0.6 g. thionyl chloride in 3 ml. of dimethylformamide. The reaction is cooled in an ice bath. The reaction is allowed to stand at room temperature overnight. Then the reaction mixture is poured into 140 ml. of cold water and the product crystallizes from solution. The product is collected by filtration and air dried, m.p. 136°-137° C.

Analysis Calcd. for $C_{13}H_{14}N_4O_4$: C, 53.79; H, 4.86; N, 19.30. Found: C, 53.43; H, 4.92; N, 19.36.

EXAMPLE 44

The selective postemergence herbicidal activity of the compounds of the present invention is demonstrated by the following tests, wherein a variety of monocotyledonous and dicotyledonous plants are treated with test compounds dispersed in aqueous-acetone mixtures. In the tests, seedling plants are grown in Jiffy ® flats for about two weeks. The test compounds are dispersed in 50/50 acetone/water mixtures in sufficient quantity to provide the equivalent of about 0.25 lb. to 4 lbs. per acre of active compound when applied to the plants through a spray nozzle operating at 40 psi for a predetermined time. After spraying, the plants are placed on greenhouse benches and are cared for in the usual manner, commensurate with conventional greenhouse practices. Three to five weeks after treatment, the seedling plants are examined and rated according to the rating system provided below. The data obtained are reported in Tables III and VI where it can be seen that the compounds are effective for the control of a variety of broadleaf weeds and grass weeds.

| Rating System: | % Difference in Growth from the Check[1] |
|---|---|
| 0 - no effect | 0 |
| 1 - possible effect | 1-10 |
| 2 - slight effect | 11-25 |
| 3 - moderate effect | 26-40 |
| 5 - definite injury | 41-60 |
| 6 - herbicidal effect | 61-75 |
| 7 - good herbicidal effect | 76-90 |
| 8 - approaching complete kill | 91-99 |
| 9 - complete kill | 100 |
| 4 - abnormal growth, that is, a definite physiological malformation but with an over-all effect less than a 5 on the rating scale. | |

[1]based on visual determination of stand, size, vigor, chlorosis, growth malformation and over-all plant appearance.

| | Plant Species Used in Evaluation | |
|---|---|---|
| Common Name | Abbreviation | Scientific Name |
| Lambsquarters | LA | Chenopodium album |
| Wild Mustard | MU | Brassica kaber |
| Pigweed | PI | Amaranthus retroflexus |
| Ragweed | RW | Ambrosia artemisiifolia |
| Morning glory | MG | Ipomoea purpurea |
| Velvetleaf | VL | Abutilon theopharasti |
| Barnyard grass | BA | Echinochloa crusgalli |
| Crabgrass | CR | Digitaria sanguinalis |
| Green Foxtail | FO | Setaria viridis |
| Wild Oats | WO | Avena fatua |
| Fall Panicum | FP | Panicum dichotomiflorum |
| Corn | CN | Zea mays |
| Cotton | CO | Gossypium hirsutum |
| Soybean | SY | Glycine max |
| Rice | RI | Oryza sativa |
| Sugarbeets | SB | Beta vulgaris |

TABLE III

POSTEMERGENCE HERBICIDAL ACTIVITY OF 1H-BENZOTRIAZOLES

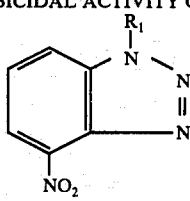

| STRUCTURE | RATE | PLANT SPECIES | | | | | | | | | | | | |
|---|---|---|---|---|---|---|---|---|---|---|---|---|---|---|
| $R_1$ | LBS./ACRE | LA | MU | PI | RW | MG | BA | CR | FO | WO | CN | CO | SY | RI |
| H | 4 | 9 | 9 | 1 | 0 | 0 | 0 | 0 | 7 | 1 | 0 | 0 | 0 | 1 |
| For comparison Lit. compound | 1 | 0 | 0 | 0 | 0 | 0 | 0 | 0 | 2 | 0 | 0 | 0 | 0 | 0 |

TABLE III-continued
POSTEMERGENCE HERBICIDAL ACTIVITY OF 1H-BENZOTRIAZOLES

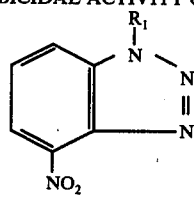

| STRUCTURE R₁ | RATE LBS./ACRE | LA | MU | PI | RW | MG | BA | CR | FO | WO | CN | CO | SY | RI |
|---|---|---|---|---|---|---|---|---|---|---|---|---|---|---|
| CH₃ For comparison Lit. compound | 4 1 | 0 0 | 1 1 | 7 0 | 0 0 | 0 0 | 9 0 | 7 0 | 5 0 | 0 0 | 1 0 | 1 0 | 1 1 | 2 0 |
| —CH₂—C₆H₅ | 4 1 0.5 | 9 9 9 | 9 9 9 | 9 9 9 | 8 3 0 | 9 9 2 | 9 6 2 | 9 9 9 | 9 7 3 | 1 1 0 | 1 0 0 | 9 9 1 | 1 0 0 | 2 1 1 |
| —CH(CH₃)₂ | 4 1 0.5 | 9 9 9 | 9 9 9 | 9 9 9 | 5 0 0 | 9 2 3 | 9 8 1 | 9 9 9 | 9 9 7 | 2 1 1 | 1 0 0 | 9 8 7 | 3 1 0 | 2 1 1 |
| —CH(C₂H₅)₂ | 1 0.5 0.25 | 9 9 9 | 9 9 9 | 9 9 .9 | 9 0 0 | 9 9 9 | 9 2 5 | 9 9 9 | 9 8 3 | 1 1 1 | 0 0 1 | 9 9 0 | 5 1 1 | 2 2 1 |
| cyclopentyl | 4 1 | 9 3 | 9 9 | 9 3 | 9 9 | 9 2 | 9 7 | 9 9 | 8 2 | 8 2 | 2 1 | 9 3 | 7 2 | 9 2 |
| —CH(CH₃)C₃H₇-n | 1 | 8 | 9 | 9 | 7 | 8 | 5 | 3 | 2 | 2 | 1 | 7 | 5 | 6 |
| —CH(CH₃)C₂H₅ | 1 0.5 0.25 | 9 9 6 | 9 9 9 | 9 9 9 | 8 2 0 | 9 9 9 | 9 9 7 | 9 8 9 | 9 8 6 | 6 3 2 | 7 7 2 | 9 9 5 | 7 3 0 | 2 2 1 |
| —C(CH₃)₃ | 4.0 1.0 0.5 | 9 7 0 | 2 3 2 | 9 8 2 | 9 0 0 | 3 3 1 | 7 3 0 | 7 5 6 | 7 2 3 | 1 1 0 | 1 1 1 | 1 0 0 | 1 0 0 | 1 0 0 |
| cyclopropyl | 2.0 1.0 0.5 | 7 7 2 | 5 8 2 | 9 9 7 | 5 0 0 | 3 3 3 | 3 5 1 | 7 7 2 | 3 2 1 | 2 2 1 | 1 | | | |
| 4-methylcyclohexyl | 2.0 1.0 0.5 | 7 5 5 3 | 9 8 5 | 9 9 2 | 8 0 0 | 9 2 2 | 6 3 1 | 6 6 6 3 | 3 1 1 | 1 0 0 | | | | |
| cyclooctyl | 1.0 0.5 0.25 | 9 5 7 | 9 9 9 | 9 9 9 | 9 7 0 | 9 7 9 | 9 7 7 | 9 7 7 | 8 7 7 | 6 1 2 | 3 3 3 | 3 9 3 | 9 3 3 | 7 5 5 |
| cyclohexanone | 2.0 1.0 0.5 | 9 9 3 | 9 9 7 | 9 9 9 | 9 7 0 | 9 9 9 | 7 9 3 | 8 8 5 | 6 6 1 | 2 1 1 | | | | |
| cyclohexanol | 1.0 0.5 | 8 5 | 9 9 | 9 9 | 3 3 | 9 9 | 5 3 | 3 2 | 3 1 | 2 2 | 3 3 | 9 5 | 7 3 | 5 5 |
| cyclohexyl-OCHO | 1.0 0.5 | 5 5 | 9 5 | 9 9 | 9 7 | 9 3 | 2 1 | 7 1 | 9 2 | 1 0 | 2 1 | 5 7 | 5 5 | 7 2 |
| cyclohexyl | 1 0.5 0.25 | 9 9 9 | 9 9 9 | 9 9 9 | 9 9 0 | 9 9 9 | 9 8 7 | 9 7 7 | 9 7 7 | 2 1 1 | 3 2 1 | 9 9 9 | 5 5 5 | 3 3 2 |
| —CH(C₃H₇-n)₂ | 4 1 | 9 0 | 9 5 | 9 5 | 0 0 | 2 2 | 3 1 | 7 3 | 2 1 | 1 0 | 0 0 | 1 0 | 2 1 | 1 0 |
| —CH₂-cyclohexyl | 1 0.5 0.25 | 9 9 8 | 9 8 8 | 9 9 9 | 0 0 0 | 9 9 9 | 9 7 6 | 9 7 3 | 9 7 5 | 1 1 0 | 2 1 0 | 9 7 3 | 2 1 0 | 3 3 3 |

TABLE III-continued
POSTEMERGENCE HERBICIDAL ACTIVITY OF 1H-BENZOTRIAZOLES

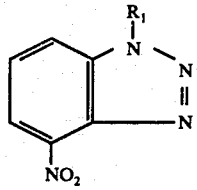

| STRUCTURE R$_1$ | RATE LBS./ACRE | LA | MU | PI | RW | MG | BA | CR | FO | WO | CN | CO | SY | RI |
|---|---|---|---|---|---|---|---|---|---|---|---|---|---|---|
| cyclohexenyl | 1 | 9 | 9 | 9 | 9 | 9 | 7 | 9 | 9 | 2 | 1 | 9 | 2 | 5 |
|  | 0.5 | 9 | 9 | 9 | 9 | 9 | 7 | 7 | 8 | 1 | 1 | 7 | 1 | 3 |
|  | 0.25 | 8 | 7 | 9 | 2 | 3 | 5 | 3 | 3 | 0 | 1 | 7 | 1 | 3 |
| cycloheptyl | 1 | 9 | 9 | 9 | 9 | 9 | 9 | 9 | 9 | 2 | 2 | 9 | 9 | 2 |
|  | 0.5 | 8 | 9 | 9 | 7 | 9 | 9 | 7 | 3 | 1 | 2 | 9 | 6 | 5 |
|  | 0.25 | 7 | 7 | 9 | 2 | 9 | 3 | 7 | 1 | 1 | 1 | 9 | 2 | 3 |
| dichlorocyclohexyl | 1 | 9 | 9 | 9 | 9 | 9 | 9 | 9 | 9 | 5 |  |  |  |  |
|  | 0.5 | 8 | 9 | 9 | 9 | 9 | 9 | 9 | 9 | 3 |  |  |  |  |
|  | 0.25 | 5 | 9 | 9 | 8 | 9 | 9 | 9 | 8 | 3 |  |  |  |  |
| methylcyclohexyl | 1 | 9 | 9 | 9 | 9 | 9 | 9 | 7 | 7 | 6 |  |  |  |  |
|  | 0.5 | 5 | 9 | 9 | 0 | 9 | 7 | 6 | 1 | 2 |  |  |  |  |
|  | 0.25 | 9 | 8 | 9 | 0 | 9 | 7 | 1 | 1 | 1 |  |  |  |  |

TABLE IV
POSTEMERGENCE HERBICIDAL ACTIVITY OF 2 H-BENZOTRIAZOLES

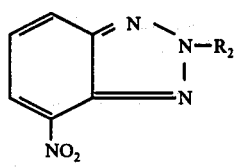

| STRUCTURE R$_2$ | RATE LBS./ACRE | LA | MU | PI | RW | MG | BA | CR | FO | WO | CN | CO | SY | RI |
|---|---|---|---|---|---|---|---|---|---|---|---|---|---|---|
| —CH(CH$_3$)$_2$ | 4 | 9 | 9 | 9 | 9 | 9 | 9 | 9 | 9 | 2 | 3 | 9 | 9 | 5 |
|  | 1 | 9 | 9 | 9 | 0 | 8 | 8 | 9 | 9 | 1 | 1 | 9 | 1 | 1 |
|  | 0.5 | 1 | 8 | 9 | 0 | 5 | 6 | 7 | 7 | 0 | 1 | 3 | 1 | 0 |
| —CH(CH$_3$)C$_2$H$_5$ | 1 | 9 | 9 | 9 | 0 | 1 | 9 | 9 | 9 | 2 | 1 | 3 | 1 | 1 |
|  | 0.5 | 9 | 9 | 9 | 0 | 3 | 8 | 9 | 9 | 0 | 1 | 2 | 1 | 1 |
|  | 0.25 | 0 | 9 | 9 | 0 | 0 | 3 | 9 | 9 | 0 | 0 | 1 | 0 | 0 |
| —CH$_2$-phenyl | 4 | 9 | 9 | 9 | 0 | 9 | 5 | 9 | 3 | 1 | 1 | 3 | 0 | 1 |
|  | 1 | 7 | 9 | 9 | 0 | 7 | 2 | 9 | 2 | 0 | 1 | 1 | 0 | 1 |
| —CH(C$_2$H$_5$)$_2$ | 4 | 9 | 9 | 9 | 5 | 9 | 9 | 9 | 9 | 1 | 2 | 9 | 3 | 1 |
|  | 1 | 9 | 3 | 9 | 0 | 9 | 8 | 9 | 9 | 1 | 5 | 9 | 3 | 1 |
|  | 0.5 | 7 | 3 | 9 | 0 | 2 | 7 | 9 | 9 | 0 | 2 | 3 | 3 | 0 |
| cyclopentyl | 4 | 9 | 9 | 9 | 9 | 5 | 9 | 9 | 7 | 3 | 2 | 2 | 2 | 5 |
| cyclohexenyl | 4 | 9 | 9 | 9 | 0 | 1 | 6 | 9 | 7 | 1 | 3 | 7 | 2 | 1 |
| cyclohexyl | 4 | 7 | 9 | 9 | 1 | 3 | 3 | 8 | 3 | 2 | 2 | 5 | 6 | 2 |
|  | 1 | 2 | 2 | 5 | 0 | 1 | 1 | 2 | 2 | 0 | 0 | 1 | 2 | 0 |

TABLE IV-continued
POSTEMERGENCE HERBICIDAL ACTIVITY OF 2 H-BENZOTRIAZOLES

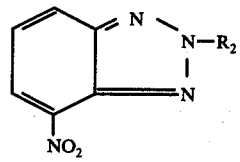

| STRUCTURE $R_2$ | RATE LBS./ACRE | PLANT SPECIES ||||||||||||
|---|---|---|---|---|---|---|---|---|---|---|---|---|---|
| | | LA | MU | PI | RW | MG | BA | CR | FO | WO | CN | CO | SY | RI |
| cyclooctyl | 4 | 7 | 7 | 9 | 0 | 6 | 6 | 6 | 2 | 3 | 2 | 3 | 3 | 3 |
| | 1 | 0 | 1 | 8 | 0 | 2 | 1 | 2 | 1 | 0 | 1 | 0 | 1 | 0 |
| 2-oxocyclohexyl | 2 | 9 | 9 | 9 | 2 | 9 | 7 | 7 | 5 | 1 | | | | |
| | 1 | 9 | 3 | 9 | 0 | 9 | 3 | 5 | 3 | 1 | | | | |
| | 0.5 | 7 | 3 | 9 | 0 | 3 | 3 | 7 | 1 | 1 | | | | |

EXAMPLE 45

The selective preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.25 to 4 pounds per acre of test compound per cup. The treated cups are then placed on greenhouse benches, watered and cared for in accordance with conventional greenhouse procedures. Three or four weeks after treatment, the tests are terminated and each cup is examined and rated according to the rating system set forth below. The herbicidal proficiency of the active ingredients of the present invention is evident from the test results which are reported in the tables below.

TABLE V
PREEMERGENCE HERBICIDAL ACTIVITY OF 1H-BENZOTRIAZOLES

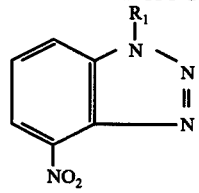

| STRUCTURE $R_2$ | RATE LBS./ACRE | PLANT SPECIES ||||||||||||
|---|---|---|---|---|---|---|---|---|---|---|---|---|---|
| | | LA | MU | PI | RW | MG | BA | CR | FO | WO | CN | CO | SY | RI |
| H For comparison Lit. compound | 4 | 0 | 0 | 0 | 0 | 0 | 0 | 0 | 0 | 0 | 0 | 0 | 0 | 0 |
| | 1 | 0 | 0 | 0 | 0 | 0 | 0 | 0 | 0 | 0 | 0 | 0 | 0 | 0 |
| $CH_3$ For comparison Lit. compound | 4 | 3 | 5 | 0 | 8 | 1 | 7 | 6 | 6 | 0 | 0 | 1 | 1 | 9 |
| | 1 | 0 | 0 | 0 | 0 | 0 | 4 | 3 | 5 | 0 | 0 | 0 | 0 | 1 |
| $-CH_2-$phenyl | 4 | 5 | 7 | 9 | 7 | 0 | 9 | 9 | 9 | 0 | 0 | 0 | 0 | 0 |
| | 1 | 0 | 0 | 7 | 0 | 0 | 7 | 8 | 0 | 0 | 0 | 0 | 0 | 0 |
| $-CH(CH_3)_2$ | 4 | 7 | 7 | 3 | 7 | 0 | 9 | 9 | 7 | 0 | 0 | 0 | 0 | 7 |
| | 1 | 0 | 0 | 3 | 0 | 0 | 6 | 5 | 0 | 0 | 0 | 0 | 0 | 1 |
| $-CH(C_2H_5)_2$ | 4 | 9 | 9 | 9 | 9 | 2 | 9 | 9 | 9 | 0 | 0 | 2 | 0 | 8 |
| | 1 | 9 | 9 | 9 | 9 | 0 | 9 | 9 | 8 | 0 | 0 | 0 | 0 | 8 |
| | 0.5 | 9 | 0 | 9 | 7 | 1 | 9 | 9 | 6 | 0 | 0 | 0 | 0 | 4 |
| $-CH(CH_3)C_2H_5$ | 1 | 8 | 0 | 8 | 8 | 5 | 9 | 9 | 8 | 0 | 0 | 0 | 0 | 9 |
| | 0.5 | 4 | 0 | 7 | 5 | 0 | 8 | 8 | 5 | 0 | 0 | 0 | 0 | 5 |
| cyclopentyl | 4 | 9 | 9 | 9 | 9 | 5 | 9 | 9 | 9 | 8 | 0 | 0 | 0 | 9 |
| | 1 | 9 | 9 | 9 | 9 | 0 | 9 | 9 | 9 | 1 | 0 | 0 | 0 | 2 |
| | 0.5 | 9 | 9 | 9 | 9 | 0 | 9 | 9 | 9 | 0 | 0 | 0 | 0 | 0 |
| $-CH(CH_3)C_3H_7$-n | 4 | 9 | 9 | 9 | 9 | 7 | 9 | 9 | 9 | 7 | 3 | 7 | 9 | 8 |
| | 1 | 8 | 9 | 9 | 9 | 0 | 9 | 9 | 8 | 0 | 0 | 2 | 2 | 7 |
| | 0.5 | 0 | 9 | 9 | 9 | 0 | 9 | 9 | 8 | 0 | 0 | 0 | 0 | 2 |
| cyclohexyl | 1 | 9 | 9 | 9 | 9 | 9 | 9 | 9 | 9 | 2 | 3 | 9 | 5 | 3 |
| | 0.5 | 9 | 9 | 9 | 9 | 9 | 9 | 9 | 9 | 1 | 2 | 9 | 5 | 3 |
| | 0.25 | 9 | 9 | 9 | 0 | 9 | 9 | 9 | 9 | 1 | 1 | 9 | 5 | 2 |

TABLE V-continued
PREEMERGENCE HERBICIDAL ACTIVITY OF 1H-BENZOTRIAZOLES
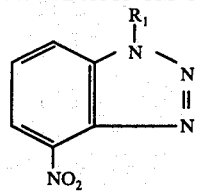
| STRUCTURE $R_2$ | RATE LBS./ACRE | LA | MU | PI | RW | MG | BA | CR | FO | WO | CN | CO | SY | RI |
|---|---|---|---|---|---|---|---|---|---|---|---|---|---|---|
| cyclohexyl | 1 | 9 | 9 | 9 | 9 | 9 | 9 | 9 | 9 | 7 | 1 | 2 | 1 | 3 |
|  | 0.5 | 9 | 6 | 8 | 9 | 0 | 9 | 9 | 9 | 4 | 0 | 0 | 0 | 3 |
|  | 0.25 | 9 | 6 | 9 | 9 | 0 | 8 | 9 | 8 | 4 | 0 | 0 | 0 | 3 |
| —CH$_2$-cyclohexenyl | 1 | 9 | 7 | 9 | 9 | 0 | 9 | 9 | 9 | 1 | 1 | 5 | 0 | 2 |
|  | 0.5 | 9 | 0 | 9 | 0 | 0 | 9 | 9 | 7 | 0 | 0 | 0 | 0 | 0 |
|  | 0.25 | 9 | 0 | 8 | 0 | 0 | 7 | 5 | 2 | 0 | 0 | 2 | 0 | 0 |
| cyclohexenyl | 1 | 9 | 7 | 9 | 9 | 2 | 9 | 9 | 9 | 0 | 1 | 0 | 0 | 7 |
|  | 0.5 | 9 | 0 | 9 | 7 | 0 | 7 | 9 | 7 | 0 | 0 | 0 | 0 | 0 |
|  | 0.25 | 7 | 0 | 7 | 0 | 0 | 6 | 5 | 2 | 0 | 0 | 0 | 0 | 0 |
| dichlorocyclohexyl | 1 | 9 | 9 | 9 | 9 | 9 | 9 | 9 | 9 | 7 | 6 | 7 | 3 | 8 |
|  | 0.5 | 9 | 9 | 9 | 9 | 9 | 9 | 9 | 9 | 3 | 6 | 3 | 2 | 7 |
|  | 0.25 | 9 | 8 | 9 | 8 | 0 | 8 | 9 | 9 | 3 | 0 | 0 | 0 | 2 |
| methylcyclohexyl | 10 | 2 | 2 | 6 | 2 | 0 | 9 | 9 | 9 | 0 | 0 | 0 | 0 | 0 |
|  | 2 | 2 | 0 | 5 | 2 | 0 | 7 | 6 | 3 | 1 | | | | |
| dimethylcyclohexyl | 1 | 9 | 9 | 9 | 9 | 2 | 9 | 9 | 9 | 7 | 2 | 6 | 0 | 7 |
|  | 0.5 | 9 | 7 | 9 | 7 | 9 | 8 | 9 | 6 | 7 | 0 | 0 | 0 | 3 |
|  | 0.25 | 9 | 3 | 8 | 5 | 0 | 6 | 9 | 5 | 2 | 0 | 0 | 0 | 1 |
| cyclopropyl | 10 | 7 | 7 | 8 | 0 | 0 | 7 | 8 | 8 | 0 | | | | |
| —C(CH$_3$)$_3$ | 4 | 7 | 5 | 7 | 9 | 1 | 8 | 9 | 9 | 0 | 0 | 2 | 0 | 1 |
|  | 1 | 7 | 0 | 5 | 7 | 0 | 3 | 0 | 0 | 0 | 0 | 0 | 0 | 0 |
| cycloheptyl | 1 | 9 | 9 | 9 | 9 | 2 | 9 | 9 | 9 | 7 | 3 | 0 | 0 | 6 |
|  | 0.5 | 7 | 0 | 8 | 8 | 0 | 9 | 9 | 9 | 4 | 0 | 0 | 0 | 1 |
|  | 0.25 | 9 | 0 | 9 | 8 | 0 | 9 | 9 | 8 | 2 | 0 | 0 | 0 | 2 |
| cyclohexanone | 2.0 | 6 | 7 | 9 | 8 | 2 | 7 | 8 | 6 | 0 | 0 | 3 | 0 | 1 |
|  | 1.0 | 3 | 0 | 9 | 5 | 0 | 5 | 7 | 1 | 0 | 0 | 0 | 0 | 0 |
| hydroxycyclohexyl | 1 | 9 | 9 | 9 | 9 | 5 | 8 | 9 | 8 | 1 | 2 | 5 | 0 | 8 |
|  | 0.5 | 8 | 8 | 9 | 8 | 2 | 7 | 7 | 7 | 0 | 2 | 5 | 0 | 7 |
|  | 0.25 | 5 | 7 | 9 | 2 | 0 | 6 | 6 | 3 | 0 | 0 | 0 | 0 | 6 |
| formyloxycyclohexyl | 1 | 9 | 9 | 9 | 9 | 2 | 8 | 8 | 9 | 2 | 3 | 3 | 5 | 9 |
|  | 0.5 | 8 | 8 | 9 | 9 | 0 | 8 | 7 | 7 | 0 | 0 | 0 | 0 | 6 |
|  | 0.25 | 7 | 8 | 9 | 6 | 0 | 7 | 6 | 6 | 0 | 0 | 2 | 0 | 3 |

TABLE VI
PREEMERGENCE HERBICIDAL ACTIVITY OF 1H-BENZOTRIAZOLES

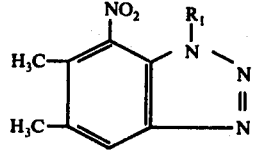

| STRUCTURE R₁ | RATE LBS./ACRE | LA | MU | PI | RW | MG | BA | CR | FO | WO | CN | CO | SY | RI |
|---|---|---|---|---|---|---|---|---|---|---|---|---|---|---|
| —CH(C₂H₅)₂ | 3 | 8 | 4 | 6 | 0 | 0 | 9 | 9 | 8 | 6 | 2 | 0 | 0 | 1 |
|  | 1 | 8 | 0 | 0 | 0 | 0 | 9 | 9 | 8 | 1 | 0 | 0 | 0 | 1 |
| *—CH(CH₃)C₂H₅ | 10 | 0 | 0 | 0 | 3 | 4 | 9 | 9 | 9 | 0 | — | — | — | — |

*Conducted as described above but at 10 lbs./acre rate.

TABLE VII
PREEMERGENCE HERBICIDAL ACTIVITY OF 2H-BENZOTRIAZOLES

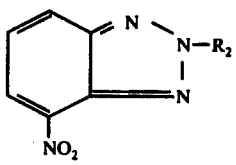

| STRUCTURE R₁ | RATE LBS./ACRE | LA | MU | PI | RW | MG | BA | CR | FO | WO | CN | CO | SY | RI |
|---|---|---|---|---|---|---|---|---|---|---|---|---|---|---|
| —CH(CH₃)₂ | 4 | 5 | 7 | 9 | 0 | 0 | 3 | 8 | 5 | 0 | 0 | 5 | 3 | 9 |
|  | 1 | 0 | 5 | 8 | 0 | 0 | 0 | 2 | 2 | 0 | 0 | 0 | 3 | 1 |
| —CH(C₂H₅)₂ | 4 | 9 | 9 | 9 | 0 | 0 | 9 | 9 | 9 | 7 | 0 | 0 | 0 | 9 |
|  | 1 | 0 | 0 | 2 | 0 | 0 | 6 | 7 | 4 | 0 | 0 | 0 | 0 | 0 |
| cyclohexenyl | 4 | 9 | 9 | 9 | 0 | 1 | 6 | 9 | 7 | 1 | 0 | 3 | 7 | 2 |
|  | 1 | 0 | 5 | 9 | 0 | 0 | 3 | 2 | 1 | 0 | 2 | 7 | 1 | 1 |

EXAMPLE 46

Preparation of 2-(4-Nitro-1H-benzotriazol-1-yl)-cyclohexanol and 2-(4-Nitro-2H-benzotriazol-2-yl)-cyclohexanol

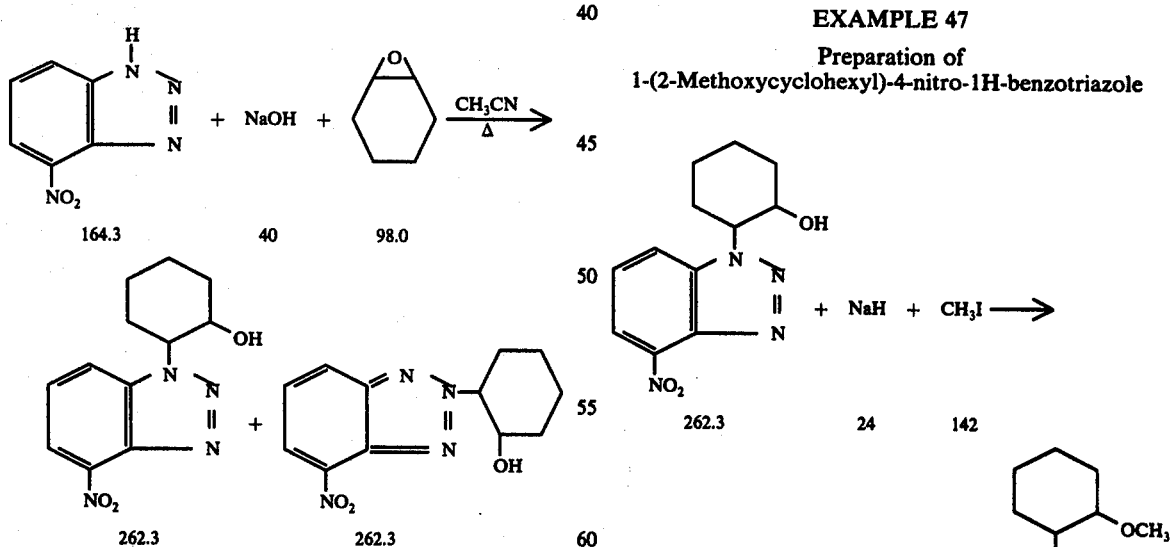

A mixture of 4-nitrobenzotriazole (60.0 g, 0.37 mol), sodium hydroxide "Pels" (16.0 g, 0.40 mol) and 1500 ml of acetonitrile was heated to 60°. The cyclohexene oxide (80.0 g, 0.81 mol) was then slowly added and the solution heated at the reflux temperature for 48 hours. After cooling, the reaction was filtered and the acetonitrile evaporated to yield an oily residue. The 2-alkyl isomer was extracted with ethyl ether leaving behind the 1-alkyl isomer as a solid.

EXAMPLE 47

Preparation of 1-(2-Methoxycyclohexyl)-4-nitro-1H-benzotriazole

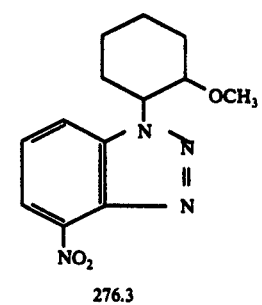

To a slurry of the hydroxy compound (3.6 g, 0.014 mol) in 100 ml of dry dimethoxyethane was added a mineral oil dispersion of 57% sodium hydride (0.85 g) at 40°. After the evolution of hydrogen had subsided, methyl iodide (6.0 g, 0.040 mol) was added over a 15-minute period. After 1½ hours, tlc indicated starting material still present and therefore additional sodium hydride (0.49 g) and methyl iodide (3.0 g, 0.20 mol) was added. After an additional 2 hours, tlc showed no starting material. The reaction mixture was filtered and the solvent evaporated to yield a dark oil. The crude product was purified by dry column chromatography using chloroform as the developing solvent. The analytical sample, m.p. 134°–136°, was recrystallized from ethanol.

EXAMPLE 48

Preparation of 4-Chloro-1-cyclohexyl-1H-benzotriazole

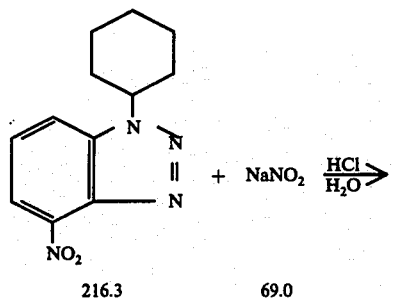

216.3     69.0

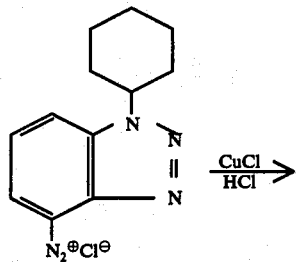

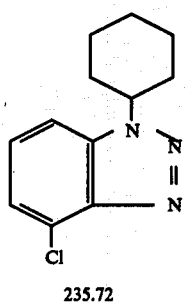

235.72

To a stirred solution of the 4-amino-1-cyclohexylbenzotriazole (11.4 g, 0.054 mol) in 75 ml of concentrated hydrochloric acid and 75 ml of water at 5°, was slowly added 4.1 g of sodium nitrite (0.059 mol) in 15 ml of water. On completion of the addition, the reaction mixture was allowed to stir an additional ½ hour at 0°–5°. Next the solution was added slowly to an excess of freshly prepared cuprous chloride in 120 ml of concentrated hydrochloric acid also at 0°–5°. On completion of the addition, the reaction came to room temperature over a 2½ hour period. Then one liter of water was added to the reaction mixture and the crude product which precipitated was collected by filtration, washed with water and air-dried. This material was purified by column chromatography to yield 6.2 g of product, m.p. 141°–144°.

EXAMPLE 49

Preparation of 4-Methoxy-1-cyclohexyl-1H-benzotriazole

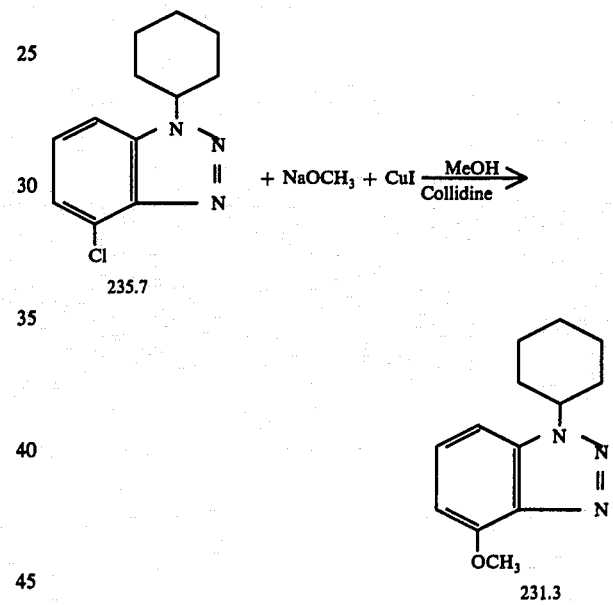

A slurry of 1.5 g of 4-chloro-1-cyclohexylbenzotriazole, 15 g of sodium methoxide, 10 g of cuprous iodide in 50 ml of 2,4,6-trimethyl pyridine (collidine) and 10 ml of methanol was heated at the reflux temperature for 26 hours. The reaction was cooled and poured into 150 ml of 10% hydrochloric acid. The product was extracted with ethyl ether and on evaporation of the solvent, 0.5 g of an oil was obtained which solidified on standing. The product had a melting point of 133°–134°.

EXAMPLE 50

Postemergence control of a variety of plant species is demonstrated for the following 1H- and 2H-benzotriazoles of the subject invention. To determine the postemergence activity of each of the test chemicals, the procedure of Example 44 is used and data obtained are reported in Tables VIII and IX below.

TABLE VIII
Postemergence Herbicidal Activity with Compounds having the Structure:

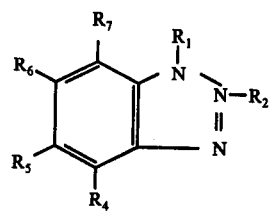

| Structure | | | | | | Rate | Plant Species | | | | | | | | | | | |
|---|---|---|---|---|---|---|---|---|---|---|---|---|---|---|---|---|---|---|
| R₁ | R₂ | R₄ | R₅ | R₆ | R₇ | lb/Acre | LA | MU | PI | RW | MG | BA | CR | FO | WO | CN | CO | SY | RI |
| —O—CO—CH₃ | H | NO₂ | H | H | H | 10 | 0 | 0 | 9 | 0 | 1 | 8 | 9 | 9 | 0 | — | — | — | — |
| cyclohexyl | H | CN | H | H | H | 10 | 9 | 9 | 9 | 8 | 9 | 9 | 9 | 9 | 6 | 5 | 2 | 9 | 5 |
| | | | | | | 4 | 9 | 9 | 9 | 3 | 7 | 7 | 6 | 6 | 3 | 3 | 7 | 8 | 5 |
| | | | | | | 1 | 9 | 9 | 9 | 0 | 8 | 3 | 3 | 3 | 2 | 3 | 7 | 7 | 5 |
| | | | | | | 0.5 | 9 | 9 | 9 | 8 | 8 | 3 | 2 | 2 | 3 | 3 | 3 | 5 | 5 |
| cyclohexyl | H | Cl | H | H | H | 10 | 9 | 9 | 9 | 9 | 9 | 9 | 9 | 9 | 9 | — | — | — | — |
| | | | | | | 4 | 9 | 9 | 9 | 9 | 8 | 8 | 9 | 9 | 9 | 5 | 7 | 9 | 7 |
| | | | | | | 1 | 9 | 9 | 9 | 9 | 9 | 9 | 9 | 9 | 9 | 6 | 7 | 7 | 7 |
| | | | | | | 0.5 | 9 | 9 | 9 | 9 | 3 | 6 | 9 | 9 | 9 | 9 | 6 | 6 | 3 |
| | | | | | | 0.25 | 9 | 9 | 9 | 9 | 0 | 6 | 9 | 8 | 9 | 2 | 9 | 7 | 3 |
| cyclohexyl | H | OCH₃ | H | H | H | 10 | 9 | 9 | 9 | 9 | 8 | 9 | 9 | 9 | 8 | — | — | — | — |
| 2-methoxycyclohexyl | H | NO₂ | H | H | H | 10 | — | 9 | 9 | 0 | 3 | 9 | 9 | 9 | 1 | — | — | — | — |
| | | | | | | 4 | — | 7 | 7 | 9 | 1 | 3 | 1 | 1 | — | 2 | 5 | 3 | 5 |

TABLE IX
Postemergence Herbicidal Activity with Compounds having the Structure:

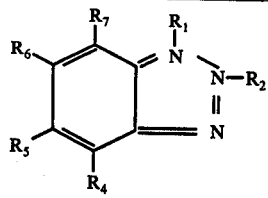

| Structure | | | | | | Rate | Plant Species | | | | | | | | | | | |
|---|---|---|---|---|---|---|---|---|---|---|---|---|---|---|---|---|---|---|
| R₁ | R₂ | R₃ | R₅ | R₆ | R₇ | lb/Acre | LA | MU | PI | RW | MG | BA | CR | FO | WO | CN | CO | SY | RI |
| H | —CH₂—phenyl | NO₂ | H | H | H | 10 | 9 | 9 | 9 | 0 | 5 | 8 | 8 | 9 | 5 | 1 | 3 | 0 | 1 |
| | | | | | | 4 | 9 | 9 | 9 | 0 | 9 | 5 | 9 | 3 | 1 | 1 | 1 | 0 | 1 |
| | | | | | | 1 | 7 | 9 | 9 | 0 | 7 | 2 | 9 | 2 | 0 | 0 | 0 | 0 | |
| H | 2-hydroxycyclohexyl | NO₂ | H | H | H | 10 | 9 | 9 | 9 | 3 | 9 | 9 | 3 | 6 | 1 | 5 | 5 | 5 | 3 |
| | | | | | | 4 | 8 | 8 | 9 | 3 | 3 | 6 | 3 | 6 | 0 | 1 | 2 | 3 | 1 |
| | | | | | | 1 | 3 | 7 | 9 | 0 | 2 | 2 | 2 | 2 | 0 | 2 | 2 | 3 | 1 |

EXAMPLE 51

The preemergence herbicidal activity of the compounds of the present invention is further demonstrated for the compounds of the present invention. Following the procedure set forth in Example 45, 1H- and 2H-benzotriazoles were evaluated for control of a variety of plant species. Data obtained are reported in Tables X and XI below.

TABLE X

Preemergence Herbicidal Activity having the Formula:

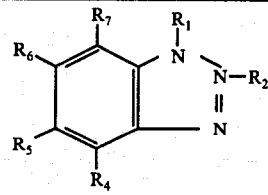

| Structure | | | | | | Rate | Plant Species | | | | | | | | | | | | |
|---|---|---|---|---|---|---|---|---|---|---|---|---|---|---|---|---|---|---|---|
| R₁ | R₂ | R₄ | R₅ | R₆ | R₇ | lb/Acre | LA | MU | PI | RW | MG | BA | CR | FO | WO | CN | CO | SY | RI |
| cyclohexyl | H | CN | H | H | H | 10 | 9 | 9 | 9 | 9 | 9 | 9 | 9 | 9 | 9 | — | — | — | — |
| | | | | | | 4 | 9 | 9 | 9 | 9 | 1 | 9 | 9 | 9 | 9 | 0 | 0 | 0 | 2 |
| | | | | | | 1 | 8 | 6 | 9 | 9 | 0 | 9 | 9 | 8 | 7 | 0 | 0 | 0 | 1 |
| | | | | | | 0.5 | 6 | 6 | 9 | 9 | 0 | 9 | 9 | 9 | 5 | 0 | 0 | 0 | 2 |
| | | | | | | 0.25 | 7 | 3 | 8 | 7 | 0 | 9 | 8 | 6 | 2 | 0 | 0 | 0 | 0 |
| cyclohexyl | H | Cl | H | H | H | 10 | 9 | 9 | 9 | 6 | 9 | 9 | 9 | 9 | 9 | — | — | — | — |
| | | | | | | 4 | 9 | 8 | 9 | 9 | 0 | 9 | 9 | 9 | 8 | 0 | 0 | 0 | 2 |
| | | | | | | 1 | 9 | 8 | 9 | 0 | 0 | 9 | 9 | 8 | 8 | 0 | 0 | 0 | 2 |
| | | | | | | 0.5 | 9 | 8 | 9 | 0 | 0 | 8 | 9 | 7 | 7 | 0 | 0 | 0 | 0 |
| | | | | | | 0.25 | 7 | 0 | 0 | 0 | 0 | 7 | 7 | 2 | 2 | 0 | 0 | 0 | 0 |
| cyclohexyl | H | OCH₃ | H | H | H | 10 | 9 | 9 | 9 | 6 | 0 | 9 | 9 | 9 | 7 | — | — | — | — |
| 2-methoxycyclohexyl | H | NO₂ | H | H | H | 10 | — | 9 | 9 | 9 | 7 | 9 | 9 | 9 | — | — | — | — | — |
| | | | | | | 4 | — | 9 | 9 | 9 | 0 | 9 | 9 | 9 | — | 0 | 8 | 0 | 8 |
| | | | | | | 1 | — | 8 | 9 | 9 | 0 | 8 | 8 | 8 | — | 0 | 4 | 0 | 3 |

TABLE XI

Preemergence Herbicidal Activity of Compounds having the Structure:

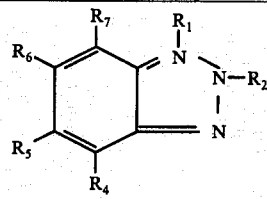

| Structure | | | | | | Rate | Plant Species | | | | | | | | | | | | |
|---|---|---|---|---|---|---|---|---|---|---|---|---|---|---|---|---|---|---|---|
| R₁ | R₂ | R₄ | R₅ | R₆ | R₇ | lb/Acre | LA | MU | PI | RW | MG | BA | CR | FO | WO | CN | CO | SY | RI |
| H | —CH₂—cyclohexyl | NO₂ | H | H | H | 10 | 0 | 0 | 0 | 0 | 0 | 6 | 8 | 7 | 0 | — | — | — | — |
| H | 2-hydroxycyclohexyl | NO₂ | H | H | H | 10 | — | 9 | 9 | 3 | 0 | 7 | 8 | 2 | 0 | — | — | — | — |
| | | | | | | 4 | 0 | 7 | 5 | 5 | 0 | 6 | 6 | 6 | 0 | 0 | 0 | 0 | 2 |

We claim:
1. A compound of the formula:

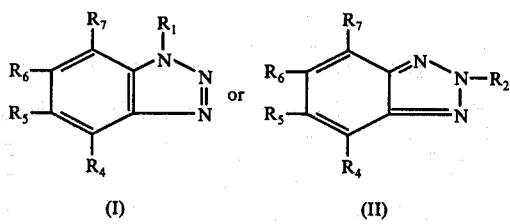

(I) or (II)

wherein R₁ and R₂ each independently represent a secondary alkyl $C_3$-$C_7$; tertiary alkyl $C_4$-$C_7$;

wherein R is $C_1$-$C_2$ alkyl; benzyl; cycloalkenyl $C_3$-$C_8$; —(CH₂)ₙ-cycloalkyl ($C_3$-$C_8$) optionally substituted with a hydroxy, alkoxy $C_1$-$C_3$, alkyl $C_1$-$C_3$ or

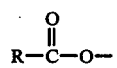

wherein R is $C_1$–$C_2$ alkyl and $n$ is 0 or 1; cyclohexylone;

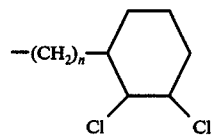

where $n$ is 0 or 1; $R_4$ represents hydrogen, chlorine, cyano, methoxy or nitro; $R_5$ and $R_6$ are both hydrogen or both methyl; $R_7$ is hydrogen or nitro; with provisos that when $R_4$ is nitro, chloro, methoxy or cyano, then $R_5$, $R_6$ and $R_7$ are each hydrogen and when $R_4$ is hydrogen then $R_7$ is nitro and $R_5$ and $R_6$ are each methyl.

2. A compound according to claim 1 wherein said compound is a formula (I) 1H-benzotriazole and $R_1$, $R_4$, $R_5$, $R_6$ and $R_7$ are as described in said claim 1.

3. A compound according to claim 1 wherein said compound is a formula (II) 2H-benzotriazole and $R_2$, $R_4$, $R_5$, $R_6$ and $R_7$ are as described in said claim 1.

4. A compound according to claim 2 wherein $R_1$ is as described therein, $R_4$ is nitro and $R_5$, $R_6$ and $R_7$ are hydrogen.

5. A compound according to claim 4 wherein $R_1$ is cycloalkenyl $C_3$–$C_8$ or —$(CH_2)_n$-cycloalkyl ($C_3$–$C_8$) optionally substituted with a hydroxy, alkoxy $C_1$–$C_3$, alkyl $C_1$–$C_3$, or

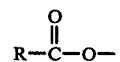

wherein R is $C_1$–$C_2$ alkyl and $n$ is 0 or 1; cyclohexylone or

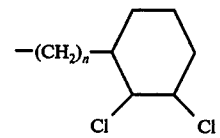

where $n$ is 0 or 1.

6. A compound according to claim 4 wherein $R_1$ is cycloalkenyl $C_3$–$C_7$.

7. A compound according to claim 4 wherein $R_1$ is a secondary alkyl $C_3$–$C_7$.

8. A compound according to claim 4 wherein $R_1$ is benzyl.

9. A compound according to claim 3 wherein $R_2$ is as described, $R_4$ is nitro and $R_5$, $R_6$ and $R_7$ are hydrogen.

10. A compound according to claim 2 wherein $R_1$ is as described; $R_4$ is hydrogen, $R_7$ is nitro and $R_5$ and $R_6$ are methyl.

11. A compound according to claim 1 1-(1-ethyl-propyl)-4-nitro-1H-benzotriazole.

12. A compound according to claim 5 1-cyclohexyl-4-nitro-1H-benzotriazole.

13. A compound according to claim 5 1-(2-cyclohexene-1-yl)-4-nitro-1H-benzotriazole.

14. A compound according to claim 5 1-cycloheptyl-4-nitro-1H-benzotriazole.

15. A compound according to claim 5 1-(2,3-dichlorocyclohexyl)-4-nitro-1H-benzotriazole.

16. A compound according to claim 5 1-cyclopentyl-4-nitro-1H-benzotriazole.

* * * * *